United States Patent [19]

Dean et al.

[11] 4,269,605

[45] May 26, 1981

[54] METHOD AND KIT FOR SEPARATION OF GLYCOPROTEINS

[75] Inventors: Peter D. G. Dean, Formby; Peter J. Brown; Vasilis Bouriotis, both of Liverpool, all of England

[73] Assignee: Amicon Corporation, Lexington, Mass.

[21] Appl. No.: 52,474

[22] Filed: Jun. 27, 1979

[30] Foreign Application Priority Data

Jun. 28, 1978 [GB] United Kingdom ............... 28195/78

[51] Int. Cl.$^3$ ..................... G01N 33/66; G01N 33/72
[52] U.S. Cl. .................................. 23/230 B; 23/901; 23/913; 260/112 B; 422/61
[58] Field of Search .................... 23/230 B, 913, 901; 422/61; 260/112 R, 112 B

[56] References Cited

U.S. PATENT DOCUMENTS 4,142,857  3/1979  Acuff ................................. 23/230 B

OTHER PUBLICATIONS

Weith et al, Biochemistry, vol. 9, 4396–4401 (1970).
Morris et al, "Separation Methods in Biochemistry", Sir Issac Pitman & Sons, Ltd., London, (1964).
Schott et al., Biochemistry, vol. 12, 932–938, (1973).
Schott, Angew. Chem. internat. Edit., vol. 11, 824–825 (1972).
Instruction pamphlet for Quik-Sep Fast Hemoglobin Test System, Isolab, Inc., Jul. 1, 1978.

*Primary Examiner*—Arnold Turk

[57] ABSTRACT

Glycoproteins, especially glycosylated hemoglobins, are separated from non-glycosylated proteins, by complexing with a dihydroxyboryl reactive agent. The resulting complex can be separated physically from the non-glycosylated protein, making possible the determination of glycosylated hemoglobin content of lysed blood; a reactive agent and a kit are described for use in such determination and as a monitor in the control of diabetic treatment. The invention can also be used preparatively to isolate glycoproteins.

8 Claims, No Drawings

METHOD AND KIT FOR SEPARATION OF GLYCOPROTEINS

This invention relates to glycoproteins, more particularly to dihydroxyboryl-glycoprotein complexes and to a method and kit for detecting, separating or determining glycoproteins using such complexes.

Glycoproteins are conjugated proteins in which (one of) the prosthetic group(s) is a carbohydrate derivative. They occur widely in nature and serve a vast number of functions. For example, glycoproteins are found in blood and secretions, in cell membranes and in connective tissue. Glycoproteins can be industrially important compounds, e.g., alkaline phosphatase is used for immunoassay and diagnostic purposes.

Of interest are the glycoproteins that occur in erythrocytes, particularly the three minor glycohemoglobins designated collectively as $HbA_1$. Further it has been established that the concentrations of these three glycoproteins are elevated in humans and animals suffering from diabetes mellitus or pregnancy. See L. A. Trivelli et al., New England Journal of Medicine, 284, 353 (1971), Koenig & Cerami, Proceedings of the National Academy of Sciences of United States of America, 72, 3687 (1975), and Koenig et al., Diabetes, 25, 1 (1976). The reason for the increase in $HbA_1$ concentration is understood to be due to persistent hyperglycemia, occurring in the uncontrolled diabetic, causing a modification of the hemoglobin A at a constant rate during the life of the red blood cell producing $HbA_1$. In the uncontrolled diabetic the proportion of $HbA_1$ may be increased three or four fold. For example a normal person may have an $HbA_1$ (glycosylated hemoglobin) concentration of 6-9% of the total hemoglobin whereas in the diabetic the concentration may be up to 20%. Thus the measurement of $HbA_1$ concentration in hemoglobin is regarded as a very useful means of assessing the severity of glucose intolerance in diabetic patients. Owing to the delay in change in $HbA_1$ concentration, the $HbA_1$ concentration for a diabetic reflects the mean blood glucose concentration for the previous month or so.

$HbA_{1c}$ is the major component of $HbA_1$ (glycohemoglobin) and is found in the normal adult erythrocyte to the extent of 4-7%. The amino acid sequence is identical to hemoglobin A, the only difference being the attachment of a hexose to the amino terminal valine of the $\beta$ chain. The formation of the compound occurs non-enzymically. First a Schiff base slowly forms between the terminal amino group and free sugar, followed by an Amadori rearrangement:

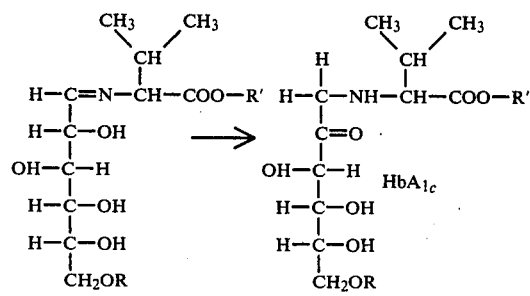

where $R'$ = Protein chain and $R = H$ or $PO_3H_2$. The properties of $HbA_{1c}$ as well as those of the other components of $HbA_1$ vary only slightly from those of normal hemoglobin.

Methods for determining the $HbA_1$ concentration in hemoglobin are generally slow and tedious, and sensitive to minor variations in pH and in ionic strength, and there is a need for a rapid, simple accurate assay. Recently Kynoch and Lehmann (The Lancet, July 2, 1977) have described a method for determination of the $HbA_1$ component of hemoglobin. This method effected separation of the $HbA_1$ component from the HbA and $HbA_2$ components by chromatography using a cationic exchange resin (Bio-rex 70, 200-400 mesh). A flow rate of 150 ml/hour was suggested which enabled the assay to be carried out in 2.5 hours. Although other versions of this method using ion exchange resin produce more rapid results, nevertheless all of the methods which depend upon the use of ion exchange resin require very precise control of pH and ionic strength.

We have now found a method for separation of glycoproteins from other proteins which is particularly suitable for use in rapidly assaying the $HbA_1$ components of hemoglobin. We have found with our novel method that assay may be achieved rapidly. Moreover, the present invention permits much greater latitude in pH and ionic strength without sacrifice of precision and accuracy.

Accordingly, in one aspect this invention provides a method for separating glycoprotein in a sample thereof which comprises contacting a dihydroxyboryl reactive substance with the sample under conditions which effect complex formation between the glycoprotein and the dihydroxyboryl moiety, separating the complexed substance from the remainder of the sample, and if desired, reacting the separated complex substance under conditions effective to recover glycoprotein.

This invention also provides a method for determining the amount of glycoprotein in a sample which comprises carrying out the above mentioned separation and measuring the amount of glycoprotein separated or recovered.

The glycoproteins separated by the process of this invention form complexes with the dihydroxyboryl moiety of an immobilized reactive agent under suitable conditions. When the carbohydrate prosthetic group of the glycoprotein contains a 1,2-diol function the complex is believed to be formed by a double condensation as shown below:

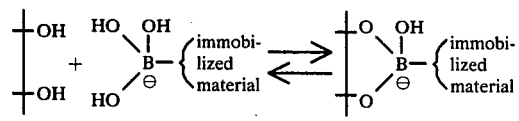

However, groups other than 1,2 could participate in such a reaction, especially 1,3 and 1,4. Accordingly it is believed not to be necessary for the glycoprotein to have vicinal diol moieties for complex formation.

The reactive agent having the dihydroxyboryl moiety or ligand can be formed from a polymeric matrix or other suitable solid or liquid support which has phenylboronic, boric or other boronic acid ligand bonded thereto or associated therewith, preferably covalently bonded thereto, in such a manner that the dihydroxyboryl moiety is available for complex formation. The reactive agent may be in liquid form so that partitioning can be used to effect separation of the complexed glycoprotein. For example an aqueous two phase system can be formed using 10% (ω/ω) polyethylene glycol—see Albertsson et al., J. Steroid Biochem., 4, 537, 1973. The reactive agent having the dihydroxy boryl moiety can be the ligand in either layer of such a two phase system, enabling partitioning of the glycoprotein to be effected.

The polymeric matrix can comprise a natural or synthetic polymeric material, particularly a hydrophilic material such as, for example, a polyacrylamide or an agarose polyacrylamide copolymer such as that sold under the trademark Ultrogel, or agarose, or a polymer having free hydroxyl groups such as cellulose, cellulose derivatives, starch, dextran and cross-linked dextran, e.g., that sold under the trademark Sephadex, proteins such as wool, or polyvinyl alcohol. The polymeric material may be cross-linked or not, or chemically modified if desired. Other polymeric materials which can be used include those sold under the trademarks Sepharose (agarose), Sephacryl (copolymer of dextran with acrylamide), or Spheron (cross-linked hydroxyethylmethacrylate), and microparticulate pellicular affinity supports such as that described in Rigopulos et al. U.S. Pat. No. 4,143,203 granted Mar. 6, 1979 (Matrex Pel 101 and 102), nylon polyesters such as polyethylene terephthalate, cellulose acetate, substituted cross-linked polystyrenes such as chloromethylated polystyrene, metal oxides, porous ceramics coated with hydrophilic organic polymers, glass or any other suitable material.

The matrix or support may take the form of beads or a sheet of fabric, e.g., woven fabric or any other convenient cast or extruded shape. In order to impart sufficient mechanical stability to the matrix it may be held in a gel tube or column or flat bed or moldable container or formed in strips of any material including dip-sticks. The method can be carried out using a column, or other technique, continuously or batchwise.

Phenylboronic, boric, or other boronic acid, such as ethaneboronic acid, 1-propaneboronic acid, 3-methyl-1-butaneboronic acid may be bound to the polymeric matrix or other suitable solid or liquid support by mechanical, physical or chemical means. The ligand may be physically held by electrostatic forces such as hydrogen bonding. Alternatively and preferably the ligand may be bonded to the matrix by means of a direct covalent bond; or it may be bonded to another molecule or molecules or aggregates of molecules of high or low molecular weight such as a whole cell, sub-cellular fraction thereof or organelle or a virus, which may be bound to the polymeric matrix either by mechanical (including entrapment), physical or chemical means. It is usually necessary that the phenylboronic, boric or other boronic acid should be bound to the matrix in such a way that it is not detached during subsequent reaction(s) leaving boronic acid hydroxyls free. If necessary, the matrix or the dihydroxyboryl ligand may be activated before coupling the two.

Examples of polymeric matrix activation prior to subsequent dihydroxyboryl ligand coupling include the use of the following substances and techniques described in the literature. The methods are listed according to functional groups on the matrix:

1. —OH group, e.g., polysaccharides.
   (a) Cyanogen halides.
   (b) Triazines.
   (c) Periodate oxidation.
   (d) p-Benzoquinone.
   (e) Bisoxiranes.
   (f) Divinylsulphone.
   (g) Epichlorohydrin.
   (h) Chloroacetic Acid and haloacetyl halides.
   (i) p-Nitrobenzyl chlorides.
2. —NH$_2$ groups, e.g., polyacrylamides.
   (a) Aminoethylation.
   (b) Deamidation to COOH.
   (c) Hydrazide.
   (d) Glutaraldehyde.
3. Si—OH groups, e.g., glass.
   (a) Silanization.
4. COOH groups, e.g., CM cellulose, Matrex Pel 101 or 2(b) above.
   (a) N-Hydroxysuccinimide esters.
   (b) Goldstein 4-centre reaction. Such methods are described in numerous publications in the literature.

Direct or indirect coupling of the dihydroxyboryl ligand to the polymeric matrix can include the reactions listed below. Such reactions are described in the literature and make use of appropriate functional groups on the ligand and matrix.
(a) Cyanogen halides
(b) Carbodiimide condensation
   (i) H$_2$O soluble
   (ii) H$_2$O insoluble
(c) Succinic anhydride
(d) Bifunctional reagents
(e) Divinylsulphone
(f) Aryl halides
(g) Alkyl halides
(h) N-(substituted) hydroxysuccinimide reaction
(i) Isothiocyanate e.g.

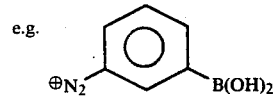

(j) Diazotization
(k) Thiolation
(l) Epichlorohydrin
(m) Periodate oxidation
(n) Mixed anhydride formation
(o) Reductive alkylation
(p) Acyl azide production Indirect coupling can include spacers between the dihydroxyboryl ligand and the matrix or support which can be hydrophilic monomers or polymers (polyethylene glycol), hydrophobic monomers or polymers (polymethylene or polyethylene imine), or aromatic bridges or any combination.

Dihydroxyboryl reactive agent can also be made by polymerizing a boronic acid derivative, e.g., dihydroxyboryl phenylacrylamide.

The dihydroxyboryl reactive agent can be used in the process of this invention by passing a suitable glycoprotein-containing sample over or through the agent or by partitioning. For example, the reactive agent can include a polymer matrix or support in the form of pellets or cylinders which can be packed into a column and a suitable glycoprotein-containing solution passed through the column. Alternatively, the sample or solution can be passed through the reactive agent including a matrix in the form of a porous sheet, or the matrix can be in the form of a dipstick, or particles contained in a porous bag, like a tea bag. Complexing of the glycoprotein with the reactive agent generally increases with increasing pH of the solvent.

To maintain aseptic conditions throughout it is occasionally found desirable to add a small quantity of an antimicrobial agent to the system which may include solvents, antibiotics and poisons. Other biochemicals, e.g., KCN in the determination of glycosylated hemoglobins, may be introduced to the glycoprotein mixture.

If the matrix or support is in the form of magnetic particles separation can be effected by use of a magnet.

Non-glycoprotein material may be eluted from a column using a suitable washing solution such as a buffer or solvent or any other biochemical reagent or electrophoretic procedure. It is usually necessary to ensure that this process does not cause the desorption of the specifically bound glycoprotein which has interacted with the reactive agent in the column or dipstick.

Recovery of the glycoprotein if desired can be achieved using some conventional desorption process, either chemical or physical, by passing the desorption-causing substance or substances over or through the reactive agent, or causing changes in pH or any other condition which formerly facilitated adsorption. Examples of suitable desorption processes include: ligand competition; inhibitor competition-specific or non-specific (such as introduction of sorbitol or sugars or other diol or alcohols which will displace the bound glycoprotein); solvent changes; buffer and/or pH changes; and ligand concentration changes.

Desorption of the polymeric matrix/boric acid, e.g., phenylboronic acid, complex is preferably done in such a manner that the dihydroxyboryl moiety is not removed from the matrix so that the matrix can be reused.

Determination of the recovered glycoprotein may be performed using any biochemical technique or by calculation of % of total protein applied using adsorbance measurements at specific wavelengths. The glycoprotein may be estimated while still complexed.

Dihydroxyboryl reactive substances are described in the literature, see for example C. H. Elliger et al., J. Chromatography, 7924 (1974). Examples are N-(m-dihydroxyborylphenyl)carbamylmethyl cellulose; boric acid gel (Aldrich Chemical Co.); [2-(diethyl)[p-(trihydroxyborato)benzyl]ammonio)ethyl]-Sephadex and other modified polymers.

This invention also provides a complex formed by reacting a dihydroxyboryl reactive agent such as hereinbefore described, preferably immobilized, and a glycoprotein.

As mentioned above this invention is particularly suitable for the separation of glycosylated hemoglobins $HbA_{1c}$, from the non-glycosylated hemoglobins such as HbA and $HbA_2$. Accordingly, the method is useful for rapidly determining the glycosylated hemoglobin content of human lysed blood as a monitor of the treatment of diabetics.

The steps involved in such a method may be summarized, simply:

1. Binding of glycosylated hemoglobin of lysed blood to immobilized or separable dihydroxyboryl reactive agent.

2. Separation of non-glycosylated hemoglobins by washing or removal of resulting complex (e.g., by removing dipstick or by partitioning).

3. Estimation of glycosylated hemoglobin either in situ on or in the reactive agent or after recovery from the reactive agent.

For example in a simple form the method can be used to assay a standard quantity of lysed blood by inserting into the lysed blood a reactive agent in the form of dihydroxyboryl ligand bonded to a dipstick. The glycosylated hemoglobin complex forms on the dipstick and is removed from the lysed blood after complete uptake. The dipstick, now colored red, after washing with buffer, is compared with a standard pre-calibrated color chart to give the % glycosylated hemoglobin in the lysed blood.

If desired the glycosylated hemoglobins can be released from the reactive agent by one of the aforementioned recovery processes, e.g., competitive inhibition using a sugar such as d-glucose. The % recovered glycosylated hemoglobin can then be estimated, e.g, by absorbance at $\lambda=413$ nm.

A suitable kit for assaying the glycosylated hemoglobin content of a blood sample includes as components: (1) a reactive agent for glycosylated hemoglobin in the lysed sample comprising a dihydroxyboryl group bonded to a support; and (2) a buffer capable of maintaining the pH of the lysed sample of blood at a pH value in the range from 7.5 to 9.0; preferably the buffer, when in solution, has an ionic strength from 0.1 to 0.5.

Preferably the kit also includes, as a third component, a lysing agent for the blood sample, e.g., a solution containing 0.1% saponin; preferably the lysing agent also contains potassium cyanide to facilitate colorimetric determination of hemoglobin and/or glycosylated hemoglobin.

In order to desorb glycosylated hemoglobin from the reactive agent for quantitation and/or to enable the latter to be reused, there may be used as elutrient a buffer of pH of less than 7.5, a buffer at pH 7.5–9 containing boric acid, or an alkyl- or aryl-boronic acid in an amount from 0.05 to 1.0 M; or, preferably, containing 0.05 to 1 M (usually 0.5 M) diol sugar, e.g., glucose, sorbitol, or ribose.

The invention is illustrated in and by the following examples:

EXAMPLE 1

(a) This example describes the determination of glycosylated hemoglobins in human lysed blood.

Phenylboronic acid was coupled to a polysaccharide, e.g., agarose in the form of beads (Sepharose 4B) by the following procedure, carried out in a fume hood:

Sepharose (20 ml. ~20 g. wet weight) is washed and cooled to 4° C. Twenty ml of cold 2 M bicarbonate-carbonate buffer (pH 11) is added and the mixture gently stirred. A solution of cyanogen bromide (2 g.) in N-methylpyrrolidone (4 ml) is cooled and slowly added to the Sepharose mixture. The mixture is stirred for 8 minutes after addition of the last of the cyanogen bromide solution. The slurry is then filtered and rapidly washed with ice cold 8% (v/v) acetone and ice cold 0.1 M bicarbonate (pH9) buffer. Excess buffer is removed from the washed slurry and then the slurry is added to a solution of m-amino phenylboronic acid (1 g.) in 20 mls. of 0.1 M bicarbonate buffer (pH9) and incubated for 18 hours at 0°–4° C. Unbound phenylboronic acid is then washed away and the polymeric matrix is packed into a 1 ml chromatography column and washed with sodium phosphate buffer pH 7.0 until all unreacted phenylboronic acid ligand is removed (as determined by U.V. monitoring of the wash solution).

(b) Five ml blood was taken from a normal individual into EDTA in a "Sequestrene" bottle and mixed gently;

a sample (0.5 ml) of this anticoagulated blood was placed into a 10 ml conical centrifuge tube and made up to 10 ml with isotonic saline. This was centrifuged at 3000 rpm for 5 minutes and the supernate decanted. The red blood cell pellet was lysed using 0.8 ml of a lysing solution containing 0.1% saponin and 0.5% KCN. After 1 minute at room temperature the lysed blood was made up to 10 ml. with sodium phosphate buffer pH 7.0 containing 0.65 g. KCN per 1 L buffer and centrifuged at 3000 rpm for 5 minutes. The supernate was collected and 2 ml of this was allowed to flow over the phenylboronic acid column described above at a flow rate of about 60 ml per hour. The eluate was collected in a 25 ml volumetric flask and the column was washed with sodium phosphate buffer until no hemoglobin could be detected in the washings. The column was desorbed using the sodium phosphate buffer containing 0.5 M d-glucose. This desorbate was collected into a 10 ml volumetric flask. For re-use the column was again equilibrated in sodium phosphate buffer pH 7.0.

The adsorbance(A) at $\lambda=413$ nm (specific for hemoglobin) was determined for both solutions and the following calculation made:

$$\frac{A413 \text{ DESORBATE} \times 100}{A413 \text{ DESORBATE} + (A413 \text{ ELUATE} \times 2.5)} = \% \text{ glycosylated hemoglobin}$$

RESULTS:
A413 DESORBATE (10 ml.) 0.018
A413 ELUATE (25 ml.) 0.092

$$\frac{0.018 \times 100}{0.018 + (0.092 \times 2.5)} = 7.25\% \text{ glycosylated hemoglobin}$$

EXAMPLE 2

This example demonstrates that the phenylboronic acid column is specific for glycosylated hemoglobin in the system described in Example 1.

Blood collected from another normal individual was treated in exactly the same manner as in Example 1 and the % glycosylated hemoglobin determined.

Blood from the same individual was determined for glycosylated hemoglobins by the method of Kynoch P.A.M. and Lehmann H (The Lancet July 2 p. 16 1977) using Amberlite Resin cg50 Type II 200 mesh substituted for the Bio-rex 70 cation exchange resin.

| RESULTS: | % GLYCO-SYLATED Hb |
|---|---|
| PHENYLBORONIC ACID METHOD OF EXAMPLE 1 | 5.34% |
| KYNOCH & LEHMANN METHOD | 5.45% |

EXAMPLE 3

This example demonstrates the specificity of immobilized phenylboronic acid for glycosylated hemoglobin using previously purified preparations.

Blood from a normal individual was determined for glycosylated hemoglobin using the method of Kynoch and Lehmann. This procedure separated hemoglobin into two distinct fractions (1) Hb glycosylated (2) Hb A+A$_2$. Both fractions were prepared according to this method and collected into sodium phosphate buffer pH 7.0 as described for use in Example 1. Each fraction was in turn offered up to the phenylboronic acid column as described in Example 1. The % recovery of both is shown in the Results.

| RESULTS: | RECOVERY |
|---|---|
| Hb A + A$_2$ (non-glycosylated) | 0.457% |
| Hb A glycosylated | 44.79% |

100% recovery was not attained with Hb A glycosylated which gives an indication that the column is saturated.

Binding of non-glycosylated hemoglobin in negligible.

EXAMPLE 4

This example illustrates the retention of a glycoprotein in the form of specific pregnancy protein 1(sp$_1$) on a phenylboronic acid Sepharose column.

(a) 1 g of CNBr activated agarose gel beads (CNBr activated Sepharose) is swollen and washed for 15 minutes on a glass filter with $10^{-3}$ M HCl solution (200 ml). Metaaminophenylboronic acid (about 10 mg) is dissolved in 0.1 M NaHCO$_3$ buffer solution containing 0.5 M NaCl (5 ml), mixed with the gel in a test tube, and the mixture is rotated end-over-end for 2 hours at 4° C. (Other gentle stirring methods may be employed, but magnetic stirrers should be used with great care to avoid fragmentation of the gel beads.) Unbound material is washed away with the coupling buffer, and any remaining active groups are reacted with 1 M ethanolamine at pH 8 for 1-2 hours. Three washing cycles are used, each cycle consisting of a wash at pH 4 (0.1 M acetate buffer containing 1 M NaCl) followed by a wash at pH 8 (0.1 M borate buffer containing 1 M NaCl).

(b) The column is equilibrated by washing with phosphate buffer pH 7.0 and then reacted with a solution containing plasma protein, in particular sp$_1$ (specific pregnancy protein 1).

All sp$_1$ was retained (as shown by polyacrylamide gel electrophoresis and radial immunodiffusion) and was eluted with sorbitol (20 mM in 0.1 M phosphate buffer=14 ml).

sp$_1$ Applied=60 mgs.
sp$_1$ Eluted=60 mgs.

EXAMPLE 5

This example illustrates the separation of the glycoprotein alkaline phosphatase from calf intestinal mucosa.

A column prepared according to Example 4(a) is washed with phosphate (or HEPES) buffer pH 8.0-8.4.

A solution containing proteins from calf intestinal mucosa, in particular alkaline phosphatase, (containing approx. 100 international units of enzyme) and 1 M NaCl was applied to the column. All alkaline phosphatase was retained by the column and after washing to remove unbound protein, the enzyme was removed by sorbitol (20 mM) pH 8.0-8.4 (HEPES buffer). Approximately 90-100% of enzymic activity can be recovered.

EXAMPLE 6

A reactive agent was prepared by washing 10 ml of agarose gel beads (Sepharose 6B) with distilled water on a sintered glass filter, and interstitial water removed by vacuum filtration. The gel was suspended in 6 ml of 1 M sodium hydroxide containing 2 mg/ml of sodium borohydride and 5 ml of 1,4-butanediol diglycidylether. The reaction was allowed to proceed overnight with slow stirring at room temperature. The gel was then thoroughly washed with distilled water at 5° C. The reaction can be represented as follows:

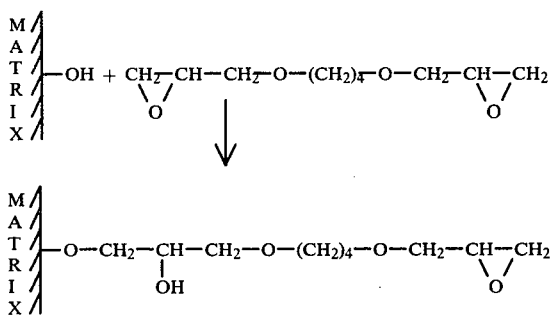

The activated product was stored for several months in the cold without significant decrease in the number of oxirane groups. Shorter reaction time, or lower concentration of bisepoxide gave a lower concentration of oxirane groups.

Other alkanediol diglycidyl ethers can be used as well for activation such as 1,3-propanediol diglycidyl ether, 1,5-pentanediol diglycidyl ether, 1,6-hexanediol diglycidyl ether, 2,5-hexanediol diglycidyl ether, and other alkanediol diglycidyl ethers or aliphatic diepoxides having 3 to 6 carbon atoms.

Coupling of the activated product with a dihydroxyboryl moiety or ligand was carried out by mixing the product with an alkaline medium, (0.2 M sodium carbonate pH 11 to 12) containing 50 to 500 mg of m-amino phenylboronic acid. High concentration of the ligand in the reactive agent was achieved by stirring at 40° C. for 24 hours. The gel was washed with copious quantities of distilled water and stored at 4° C. The reactive agent had the composition shown below:

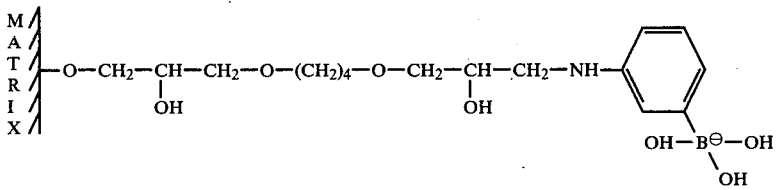

This reactive agent is superior to others in that it is free from other charged groups, by virtue of its method of preparation. Such other charged groups can lead to unwanted ion-exchange properties in the agent. From analysis of the washings it was estimated that the amount of phenylboronic acid bound to the agarose gel was approximately 20 mg/ml.

Other amino-substituted alkyl- or aryl-boronic acids can be substituted for m-aminophenylboronic acid.

A blood sample was obtained and treated as described in Example 1 (b) except that the lysing solution was combined with the phosphate buffer. The supernate was estimated to contain 10–12% hemoglobin at pH 6.7.

A specimen (0.5 ml) of the blood sample was allowed to flow over a column containing 2 ml of reactive agent prepared as described in this Example at the rate of 20 ml per hour. The column was then eluted with a 0.1 M phosphate buffer.

Several columns were prepared, each containing 2 ml of reactive agent prepared as described in this Example. A specimen (0.5 ml) of the blood sample was allowed to flow over each column at the rate of 20 ml/hr. Each column was eluted with 0.1 M phosphite buffer at a different pH to determine the percentage hemoglobin bound, which was determined by absorbance measurements at 413 nm or at 540 nm, with the following results:

| Column | Buffer pH | Percentage Bound |
|---|---|---|
| 1 | 6.6 | 3 |
| 2 | 7.3 | 6.5 |
| 3 | 7.9 | 7.3 |
| 4 | 8.9 | 7.1 |
| 5 | 6.0 | 2.2 |

The effect of increased salt concentration in the buffer was determined by employing buffers containing in addition 0.5 M KCl with the following results:

| Column | Buffer pH | Percentage Bound |
|---|---|---|
| 1 | 6.6 | 0.5 |
| 2 | 7.3 | 1.2 |
| 3 | 7.9 | 1.9 |
| 4 | 8.5 | 5.6 |
| 5 | 8.9 | 5.5 |

It will be seen that over a wide range of ionic strengths (both in the presence and the absence of added salt), the reactive agent gives a quite consistent assay at pH values between about pH 8.0 and pH 9.0. At 0.1 M ionic strength, binding is constant at pH values between about pH 7.5 and 9.0. Even at relatively high hemoglobin concentrations in the specimen applied to these columns no saturation of the columns was observed, although application of less than about 2 mg hemoglobin per column gave undesirable results. Variation in flow rate from 5 to 30 ml/hr and in temperature from 4° to 23° C. had no effect upon the percentage bound.

The columns of this Example were also found to bind glucose, which can be used as a competing ligand in a suitable buffer for desorbing the glycosylated hemoglobin. The columns can also be desorbed with 0.1 M phosphate buffer at pH 8.5 containing 0.1 M boric acid.

What is claimed is:

1. The method of separating glycoproteins from non-glycosylated proteins in a mixture which comprises bringing said mixture into contact with reactive agent comprising a dihydroxyboryl group bonded to a support to form a glycoprotein-dihydroxyboryl complex, and separating said complex from said mixture.

2. The method as claimed in claim 1 in which said dihydroxyboryl group is covalently bonded to said support.

3. The method as claimed in claim 2 in which said glycoprotein is glycosylated hemoglobin.

4. The method of assaying blood for glycosylated hemoglobin which comprises lysing a sample of blood, separating cellular debris from said lysed sample, buffering said lysed sample to a pH in the range between about 7.5 and 9.0, bringing said lysed sample into contact with a selective agent comprising a dihydroxyboryl group covalently bonded to an agarose support to form a complex of said dihydroxyboryl group with glycosylated hemoglobin in said sample, separating said complex from said sample, and determining the amount of glycosylated hemoglobin in said complex.

5. The method as claimed in claim 4 in which the amount of glycosylated hemoglobin is determined colorimetrically.

6. A kit for assaying the glycosylated hemoglobin content of a blood sample comprising as components (1) a reactive agent for glycosylated hemoglobin comprising a dihydroxyboryl group bonded to a support, (2) a buffer capable of maintaining the pH of said sample of blood at a value in the range between about 7.5 and 9.0, and (3) a supply of lysing agent for lysing said blood sample.

7. A kit as claimed in claim 6 in which said support comprises agarose in finely divided form and said dihydroxyboryl group is covalently bonded thereto.

8. A kit as claimed in claim 7 in which said dihydroxyboryl group is covalently bonded to said agarose by reacting said agarose with an aliphatic diepoxide having 3 to 6 carbon atoms and with an aminophenylboronic acid.

* * * * *